(12) United States Patent
Ringuette et al.

(10) Patent No.: US 9,637,772 B2
(45) Date of Patent: May 2, 2017

(54) ORGANIC-INORGANIC NANOFLOWERS, THEIR SYNTHESIS AND USE

(71) Applicant: AEREUS TECHNOLOGIES INC., Burlington (CA)

(72) Inventors: Maurice Ringuette, Pickering (CA); Valerian Pershin, Mississauga (CA); Heldder Gutierrez, Toronto (CA)

(73) Assignee: AEREUS TECHNOLOGIES INC., Oakville, ON (CA)

( * ) Notice: Subject to any disclaimer, the term of this patent is extended or adjusted under 35 U.S.C. 154(b) by 0 days.

(21) Appl. No.: 15/167,498

(22) Filed: May 27, 2016

(65) Prior Publication Data

US 2016/0273021 A1  Sep. 22, 2016

Related U.S. Application Data

(62) Division of application No. 14/030,764, filed on Sep. 18, 2013, now Pat. No. 9,353,384.

(60) Provisional application No. 61/704,222, filed on Sep. 21, 2012.

(51) Int. Cl.

| | | |
|---|---|---|
| *A61K 33/34* | (2006.01) | |
| *C12Q 1/10* | (2006.01) | |
| *C12P 3/00* | (2006.01) | |
| *C12N 9/96* | (2006.01) | |
| *C12N 11/14* | (2006.01) | |
| *C12N 1/20* | (2006.01) | |

(52) U.S. Cl.
CPC ............ *C12Q 1/10* (2013.01); *C12N 1/20* (2013.01); *C12N 9/96* (2013.01); *C12N 11/14* (2013.01); *C12P 3/00* (2013.01)

(58) Field of Classification Search
CPC .......... A61K 33/34; A61K 33/42; C12R 1/19
See application file for complete search history.

(56) References Cited

U.S. PATENT DOCUMENTS

2008/0081016 A1  4/2008  Peng et al.
2011/0171396 A1  7/2011  Pershin et al.

OTHER PUBLICATIONS

Ho W.H., et al., Three-dimensional crystalline SIC nanowire flowers, Nanotechnology 2004; 15:996.
Se J., Lei J., and Zare R. 2012 Protein-inorganic hybrid nanoflowers, Nature Nanotechnology. 7:428-432.
Grass G., Rensing C., and Solioz M. Metallic copper as an antimicrobial surface, Applied and Environmental Microbiology 2011: 77: 1541-1547.
Anselme K., Davidson R, Popa AM, Giazzon M., Liley M., and Ploux L. 2010. The interaction of cells and bacteria with surfaces structured at the nanometre scale. Acta Biomater. 10; 3824-3846.
Pratt L.A. and Kolter R. 1998. Genetic analysis of *Escherichia coli* biofilm formation: roles of flagella, motility, ahemotaxis and type I pili. Molecular Microbiology. 30:285-93.
Flemming H.C. and Wingender J. 2010. The biofilm matrix. Nature Reviews Microbiology. 8(9):623-633.
Mitik-Dineva N., Wang J., Truong VK., Stoddart P., Malherbe F., Crawford R.J., and Ivanova EP. 2009. *Escherichia coli, Pseudomonas aeruginosa* and *Staphylococcus aureus* Attachment Patterns on Glass Surfaces mith Nanoscale Roughness. Current Microbiology. 58:268-273.
Espirito Santo, C. et al. Contribution of copper ion resistance to survival of *Escherichia coli* on metallic copper surfaces. Applied and Environmental Microbiology. 2008; 74:977-986.
Warnes, S.L. Biocidal efficacy of copper alloys against pathogenic enterococci involves degradation of genomic and plasmid DNAs. Applied and Environmental Microbiology 2010; 5390-5401.

*Primary Examiner* — Ruth Davis
(74) *Attorney, Agent, or Firm* — Lynn C. Schumacher; Stephen W. Leonard; Hill & Schumacher

(57) ABSTRACT

Organic-inorganic nanoflowers, methods of synthesis, and uses of the nanoflowers are described. It has been found that organic-inorganic nanoflowers can be grown in the presence of a solid substrate containing copper without the requirement for added copper ion. The method includes exposing bacteria to a solid substrate containing copper in the presence of an aqueous solution that contains phosphate ions. The aqueous solution can additionally contain chloride ions, similar to that of a phosphate-buffered saline composition. The solid substrate can be an alloy of copper and tin, and the substrate can have phosphorus incorporated into it.

7 Claims, 3 Drawing Sheets

ORGANIC-INORGANIC NANOFLOWERS, THEIR SYNTHESIS AND USE

RELATED APPLICATION

This application is a divisional application of U.S. patent application Ser. No. 14/030,764, filed on Sep. 18, 2013, which claims the benefit of U.S. Provisional Patent Application Ser. No. 61/704,222 filed Sep. 21, 2012.

FIELD OF THE INVENTION

This invention relates to organic-inorganic nanoflowers, methods of synthesis, and use thereof.

BACKGROUND OF THE INVENTION

Nanostructures having a variety of structures have been known for some time. In particular, nanoflowers were first described by Ho et al. in 2004 [1]. Nanoflowers of various materials have since been described in the patent literature. See, for example, United States Patent Publication No. 2008/0081016 [2]. Apparently, all known nanoflowers were of an inorganic composition until Ge described hybrid organic-inorganic nanoflowers in 2012 [3]. Ge describes various nanoflowers, all of which are described as being composed of $Cu_3(PO_4)_2 \cdot 3H_2O$, the organic portion varying from type to type, but being an enzyme e.g., BSA (bovine serum albumin), α-lactalbumin, laccase, or carbonic anhydrase, in each case. Ge formed nanoflowers in a liquid medium containing phosphate buffered saline (PBS) and $CuSO_4$ in the presence of an enzyme. Ge stated that the chloride ion of the PBS was important in nanoflower formation by preventing precipitation of copper as copper phosphate i.e., to maintain the availability of copper in its ionic form for formation of the nanoflowers, postulating that the chloride component of PBS plays the role of forming soluble $Cu^{2+}$ chloride complexes.

SUMMARY OF THE INVENTION

The inventors have found that organic-inorganic nanoflowers can be grown in the presence of a solid substrate containing copper without the requirement for added copper ion.

An aspect of the invention is a method for the production of nanoflowers. The method comprises exposing bacteria to a solid substrate comprising copper in the presence of an aqueous solution comprising phosphate ions.

Preferably, the aqueous solution additionally contains chloride, similar to that of the phosphate-buffered saline composition of the examples, described below.

In an exemplary embodiment, the solid substrate is an alloy of copper and tin.

A copper-tin alloy can include up to about 40% by weight of tin, or up to about 35%, or up to about 30%, or up to about 25%, or up to about 20%, or up to about 15%, or up to about 10%, or up to about 5% by weight of tin. A copper-tin alloy can include at least about 5% by weight tin, or at least about 10%, or at least about 15%, or at least about 20%, or at least about 25%, or at least about 30% by weight tin.

In embodiment, the copper-tin alloy can include between about 5% and 30% tin by weight, or between about 5% and 25%, or between about 5% and 20%, or between about 5% and 15%, or between about 5% and 10% by weight tin, or about 5%, or about 6%, or about 7%, or about 8%, or about 9% or about 10% by weight tin.

The solid substrate may include phosphorus with the copper, and may included in a copper-tin alloy. Phosphorus content of the solid substrate can be up to about 2% by weight of the substrate, or up to about 1% by weight of the substrate, and/or at least 0.5% by weight of the substrate.

The copper content of the solid substrate can be at least about 60% by weight, or at least about 65%, or at least about 70%, or at least about 75%, or at least about 80%, or at least about 85%, or at least about 90%, or at least about 95%. The copper content of the solid substrate can be up to about 95% by weight, or up to about 90%, or up to about 85%, or up to about 80%, or up to about 75% by weight of the solid substrate.

In embodiments, the copper content of the solid substrate is between 60% and 95% by weight, or between about 65% and 95% by weight, or between about 70% and 95% by weight, or between about 75% and 95% by weight, or between about 80% and 95% by weight, or between about 85% and 95% by weight, or between about 90% and 95% by weight.

The surface of the substrate to which the bacteria is exposed is preferred to have a surface roughness, $R_a$, of at least about 8 μm, or at least about 10 μm, or at least about 12 μm, or about 8, 9, 10, 11, 12 or 13 μm.

The surface also preferably has a $R_v$ of no greater than about 30 μm, or no greater than about 29 μm, 28 μm, 27 μm, 26 μm, 25 μm, 24 μm, 23 μm or 22 μm, or wherein said surface has a $R_v$ of about about 22, 23, 24, 25, 26, 27, 28, 29, 30 or 31 μm.

In an exemplary embodiment, the bacteria is a gram negative bacterium, and can be *E. coli*.

The solution in which the nanoflowers are grown typically has a pH of between 7.0 and 7.4.

Chloride ions, when present, are typically present in the solution in a concentration of about 1.5 mM, and nanoflowers are formed within about 2 hours of the bacteria initially being exposed to the substrate.

The invention also includes a method for the production of nanoflowers that are functionalized with a protein or polypeptide, which may have enzymatic activity. Usually, the active substance e.g., enzyme is an isolated enzyme and is present in the aqueous growth solution at a concentration sufficient for the enzyme to be incorporated into the nanoflowers. An "isolated" substance such as a protein, polypeptide, enzyme, etc. is one that can be obtained from its natural source, can be produced using recombinant DNA technology, or can be produced by chemical synthesis. The term does not necessarily reflect the extent to which a substance has been purified, but indicates that the substance has been separated from components that naturally accompany it. In this way, the functional activity of the substance is conferred on the nanoflower material into which it is incorporated.

Enzymes that can be include as part of the composite material of the nanoflower include, but are not limited to, laccase, α-lactalbumin, carbonic anydrase, and lipase.

Another aspect of the invention is a method of detecting the presence of gram-negative bacteria in a sample. The method includes:

exposing the sample to a solid substrate comprising copper in the presence of aqueous solution comprising phosphate and chloride ions for a predetermined amount of time; and subsequently visually determining the presence or absence of nanoflowers on the surface, wherein the presence of nanoflowers indicates the presence of the bacteria in the sample.

The invention can include fixing the bacteria.

The method can include visually determining the presence or absence of nanoflowers by examining the substrate surface microscopically.

A composite material of the invention includes a nanoflower and bacterium where at least a portion of the bacterium is embedded in the nanoflower.

The nanoflower portion of the material is $Cu_3(PO_4)_2$ in a preferred embodiment.

In an exemplary embodiment, composite material is anchored to a substrate wherein the substrate comprises a copper alloy.

A composite material can include an enzyme anchored to the nanoflower.

Where such an enzyme is laccase, the invention includes use of the material for the detection of a phenol in a sample.

The invention is also a method of screening a bacterium for potential to nucleate nanoflowers, the method comprising:

exposing the bacterium to growth conditions in the presence of a solid substrate as described here;

plating the face of the substrate on a transfer medium; and testing the medium for the presence of the bacterium.

A suitable medium is agar.

BRIEF DESCRIPTION OF THE DRAWINGS

Embodiments of the invention will now be described, by way of example only, with reference to the drawings, in which.

DETAILED DESCRIPTION OF THE INVENTION

Figure 1:
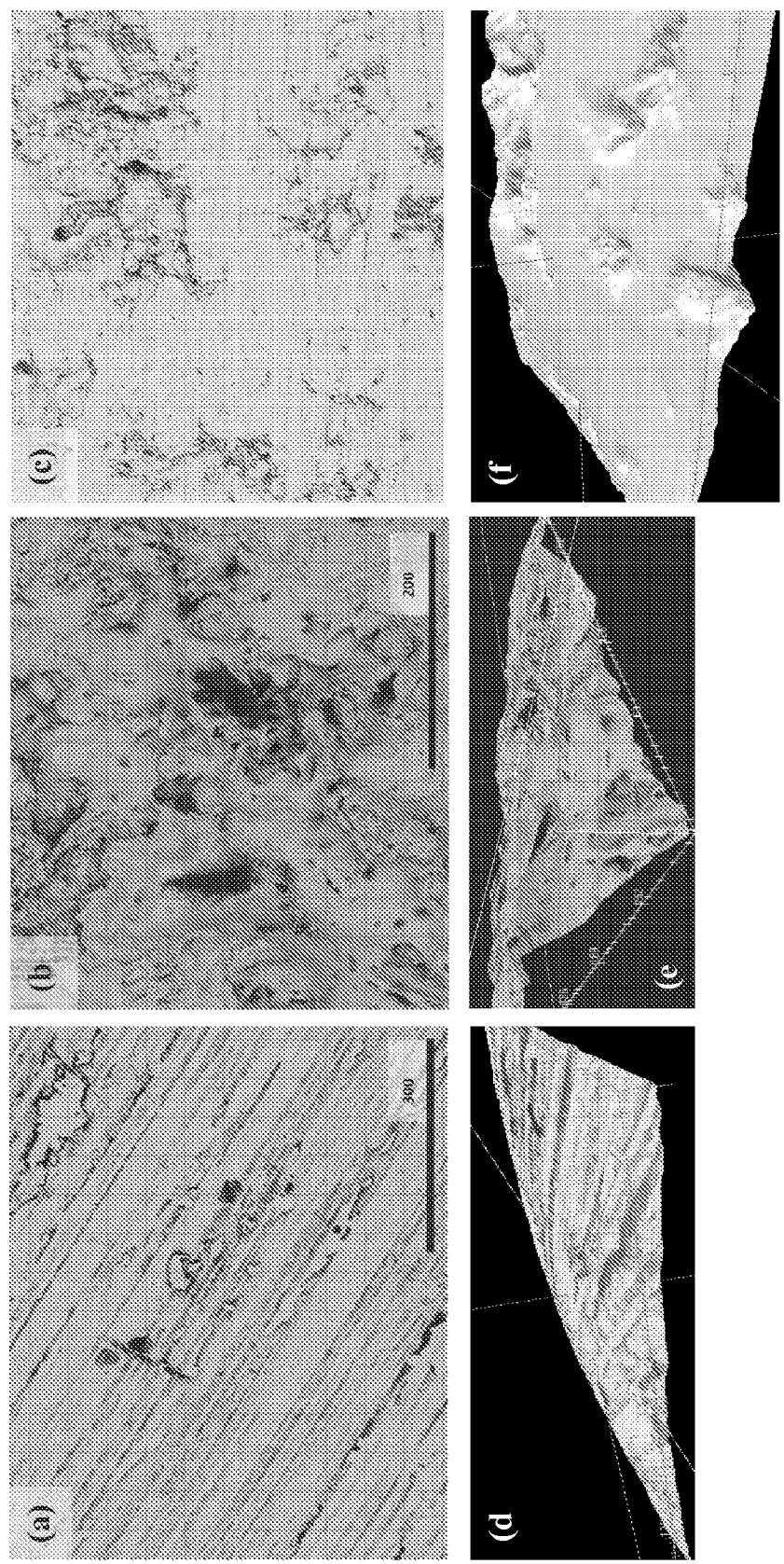
FIG. 1 shows an SEM analysis of surface topographies. (A and D) Brass sheet metal, (B and E) unsanded phosphorous bronze-MDF, (C and F) sanded phosphor bronze-MDF.

As required, embodiments of the present invention are disclosed herein. However, the disclosed embodiments are merely exemplary, and it should be understood that the invention may be embodied in many various and alternative forms.

The figures are not necessarily to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention.

As used herein, the term "about", when used in conjunction with ranges of dimensions, velocities, temperatures or other physical properties or characteristics is meant to cover slight variations that may exist in the upper and lower limits of the ranges of dimensions as to not exclude embodiments where on average most of the dimensions are satisfied but where statistically dimensions may exist outside this region.

In experiments directed to studying antimicrobial effects of various copper alloy substrates on bacteria, the inventors found bacteria resistant to transfer to agar plates during viability studies. Upon further examination, nanoflowers in which bacteria were embedded were discovered to be found anchored to substrate materials.

Nanoflowers are identifiable by microscopy, for example, scanning electron microscopy (SEM). "Nanoflowers" have typical petal-like structures, or sheets, as shown in the prior art, a nanoflower having several such sheets arranged in a generally compact structure in which they are connected together and generally arranged, in cross-section, around a central axis [1-3]. Although referred to as nanoflowers, the petals together form structures that extend into the "micro" range i.e., greater than 1000 nm, but the petal of a nanoflower has a thickness in the nano-range. Nanoflower sheets of the invention generally comprise crystalline material e.g., $Cu_3(PO_4)_2$. Nanoflowers obtained herein had a typical overall spherical shape with diameters in the range of about 3.5 to 5 μm.

A solid substrate of the invention has a metal alloy surface that includes a significant copper component, being at least 60% by weight of the alloy. The particular alloy of a substrate used in the examples is known as phosphor bronze, and contained about 91.7% copper, 7.5% tin and 0.8% phosphorus, all percentages being by weight (wt/wt %).

In embodiments, a particular "roughness" of a substrate surface is designated. Roughness is defined by the parameter "$R_a$", the absolute average deviation from the mean line of surface height (or depth) on the sampling length. The roughness of a surface can be further delimited by the parameter $R_v$, the maximum profile valley depth of a surface.

Initially, a plate count method was used to evaluate biocidal efficacy of the surfaces. Quantitative evaluation of the biocidal efficacy revealed that greater than 80% of the *E. coli* and *S. epidermis* were killed by exposure to brass sheet metal, and less than 20% with stainless steel. However, no live cells were observed on LB agar plates for either of the phosphor bronze coatings.

Surface biocidal activity was thus assessed by epifluorescence microscopy to differentiate between living and dead bacteria. After two hours exposure at room temperature in phosphate buffer (PBS), contact killing of gram-negative *Escherichia coli* and gram-positive *Staphylococcus epidermidis* by brass sheet metal and phosphor bronze was 3 to 4 times higher than a stainless steel control. Scanning electron microscope observations revealed that the surface membranes of both bacterial strains were slightly more irregular when exposed to brass sheet metal than stainless steel. However, when exposed to phosphor bronze coating, *E. coli* were 3 to 4 times larger with irregular membrane morphology. In addition, the majority of the cells were associated with spherical carbon-copper-phosphate crystalline nanostructures characteristic of nanoflowers. The membranes of many of the *S. epidermidis* exhibited blebbing and a small subset were also associated with nanoflowers. The results indicated that increasing the surface roughness of copper alloys had a pronounced impact on the membrane integrity of gram-positive and, to a lesser degree, gram-negative bacteria. Moreover, in the presence of phosphate-buffered saline, carbon-copper-phosphate-containing nanoflowers were formed on the phosphor bronze alloy having a roughened surface, likely nucleated by components derived from killed bacteria. The intimate association of the bacteria with the nanoflowers and phosphor bronze coating likely contributed to their non-reversible adhesion.

Materials and Methods

Copper Alloys

Thermally sprayed coatings have a rough surface topography with a high surface area due to coating formation by solidified multiple splats. Peaks and valleys of the coatings are random, and the surface features are most often characterized by the parameter $R_a$, the arithmetic average of the absolute values of peaks and valleys along the sampling length. Phosphor bronze was used. The coating was deposited onto medium density fiberboard (MDF), a common material for manufacturing furniture for diverse use. This process is described, for example, in United States Patent Publication No. 2011/0171396 [4]. The coating surface was sanded to reduce $R_a$ up to 3 times. The maximum profile valley depth ($R_v$) also was reduced from $R_v$=47 μm for as deposited coating to $R_v$=22 μm after sanding. Brass sheet metal with a regular striated pattern from machining has a lower surface roughness the thermal sprayed alloys. The molecular composition of the copper alloys was performed by EDS (Quantax 70 from Bruker Nano GmbH.). Surface topography measurements were performed with a diamond stylus profilometer (Surfometer 400, Precision Devices, Milan, Mich.). All 3D surface images were obtained by merging four ESM images taken at different angles using 3D-Image Viewer (Denshi Kougaky Kenkyusyo Co.)

Bacterial Strains Growth Conditions and Live/Dead Staining

Inoculations were prepared by suspending a bacterial colony in 10 ml of sterile LB broth that was kept on a rotary shaker for 24 hours at 37° C. Bacteria were then regrown for 3 hours on fresh sterile LB broth until log phase. The bacteria were added on to the substrates in order to allow for culture for 2 hours.

*E. coli* or *S. Epidermidis* were incubated for 2 hours at room temperature; substrates were stained with LIVE/DEAD Baclight viability kit (Invitrogen). SYTO 9, a green fluorescent nucleic acid stain and propidium iodide (PI), a red fluorescent nucleic acid stains were used for determination of viable bacteria. When SYTO 9 was used independently it was able to label all the bacteria due to cell permeability properties shared by these two dyes. Propidium iodide is not cell permeable and hence is only able to stain cells where the membrane has been disrupted, indicating nonviable cells. The co-stain was prepared by mixing 30 μl of SYTO 9 and 30 μl of propidium iodide, diluting this solution to 1/200 in distilled water. 6 μl of the dye was poured on each substrate where the bacteria were inoculated. The staining was kept in the dark for 15 minutes. After that, the substrates were rinsed with distilled water. The fluorescent bacteria were visualized using fluorescence with Zeiss SteREO Discovery V20.

Bacterial counts were performed by counting individual fluorescent spots within three random fields of view per sample at 120× magnification. SEM analysis revealed that a fluorescence spot 9.5 μm$^2$ was representative of one bacterium, making it feasible to count individual cells. Large, irregular shape fluorescence stains were not counted. Dividing propidium iodide red fluorescence by SYTO9 green fluorescence staining of individual bacteria quantitated lethality.

Analysis of Bacterial Morphology

After inoculation for 2 hours on a copper alloy surface bacterial cells were fixed using 4% of formaldehyde in PBS buffer. Fixation was kept overnight at 4° C. under rotating motion. Samples were then washed with PBS three times. The samples were then post fixed using 1% osmium tetroxide for 1 hour at room temperature. The osmium tetroxide was then washed off with 0.1 M PBS three times for five minutes. The samples were then dehydrated in 50%, 70%, 80%, 90% and 100% ethanol for 5 minutes, 10 minutes, 10 minutes, 15 minutes, and 2×10 minutes respectively. Chemical critical point drying was achieved using hexamethyldisilizane series (HMDS) at 3:1, 1:1, and 1:3 parts ethanol to HMDS. Each treatment was kept for 30 minutes and two changes of 100 HMDS were used for 15 minutes. The last change of HMDS was left to volatilize overnight in sterile petri dish.

For SEM observations (Hitachi 52500) samples were then sputter coated with gold-palladium.

The statistical program Graphpad® Prism was used to calculate significant difference among results. The Kruskal-Wallis test was used with a Dunn modification testing for multiple sample comparisons.

Results

Quantitative evaluation of biocidal activity performed by the direct observation of bacteria on the metal surfaces by epifluorescence microscopy using SYTO 9 and propidium iodide stains indicated a lethality ratio of 0.19 for *E. coli* and *S. epidermidis* after a two-hour exposure to control stainless steel. By comparison, *E. coli* lethality ratios of 0.66, 0.75 and 0.81 were observed for brass sheet metal and unsanded and sanded coating surfaces, respectively. Lethality ratios of 0.68, 0.85 and 0.74 for *S. epidermidis* were observed on brass sheet metal and on unsanded and sanded coatings, indicating comparable biocidal efficacies by the different copper alloy surfaces for gram-negative and gram-positive bacteria. Statistically significant differences in lethality were only observed between stainless steel and the copper containing alloys.

Surface topography is known to have a role in the adherence of microbes to their substrates. To determine differences between the bacterial adhesions to the brass and stainless steel sheet metals compared with the coated materials, surface topography was analyzed. $R_a$ measurement revealed that surface roughness of 0.18 μm for stainless steel, 0.54 μm for brass sheet metal, 12.85 μm for unsanded phosphor bronze, and 4.3 μm for sanded phosphor bronze. Consistent with the large variation in $R_a$ values, scanning electron microscopy revealed a relatively smooth, striated surface for brass sheet metal (FIG. 1*a*) compared to the highly variable topographical appearance of unsanded (FIG. 1*b*) and sanded (FIG. 1*c*) coatings. Three-dimensional analysis of the SEM images highlighted the different degrees of surface roughness between brass sheet metal (FIG. 1*d*) and the unsanded coating (FIG. 1*e*). Sanding of the coating reduced roughness by removing the peaks, leaving valleys intact (FIG. 1*f*).

To further investigate why the bacteria were not released from the phosphor bronze coating, SEM was used to observe the morphology of the cells after a two-hour incubation. The majority of *E. coli* on the control stainless steel was typically rod-shaped with smooth surfaces (FIG. 2*a*). Similarly, the surfaces of the spherical *S. epidermidis* appeared smooth (FIG. 2*d*), indicating that control stainless steel had no significant impact on the morphology of gram-negative and gram-positive bacteria. In contrast, the surface morphology of *E. coli* and *S. epidermidis* was slightly more irregular when exposed to the brass sheet metal (FIGS. 2*b* and 2*e*). There was a dramatic increase of the surface roughness and a 3 to 4 fold increase in the size of *E. coli* (FIG. 2*c*) exposed to the phosphor bronze coatings with a minor subset lysed. The majority of *E. coli* appeared to be in intimate contact or enclosed by porous spheres after two hours with an average size of 3.5-5 μm (FIG. 2c), similar in size and appearance to hybrid organic-inorganic structures that were described by Ge et al. [3]. EDS analysis of these structures revealed that they are composed of 47.0% carbon, 30.5% copper, 14.4% phosphorus, and 8.0% oxygen. Sphere-free regions of the phosphor bronze coating were composed of 95.6% copper and 4.8% phosphorus, indicating that the carbon atoms associated with the spheres were likely derived from components of killed E. coli. The porous spheres thus appeared similar in structure and composition to the protein-$Cu_3(PO_4)$·$H_2O$ nanoflowers reported by Ge et al. [3].

Figure 2:
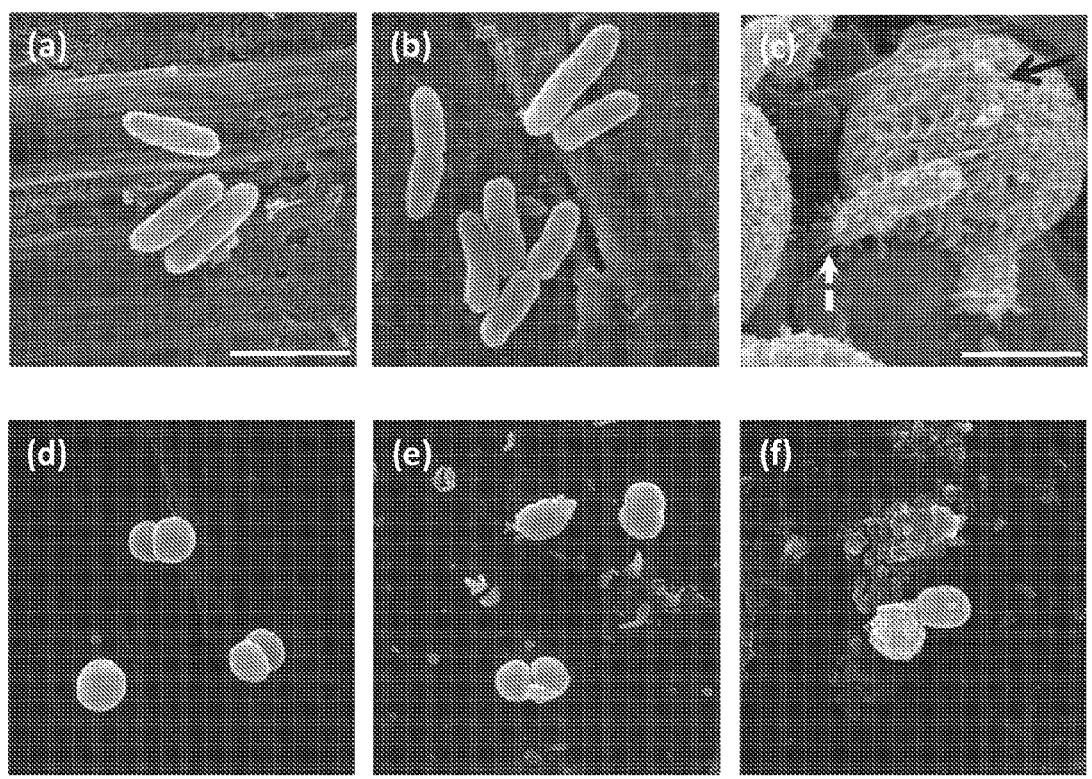
FIG. 2 shows an SEM analysis of bacterial morphology following exposure to copper alloys. (A-C) *E. coli* and (D-F) *S. epidermidis* inoculated on (A and D) steel sheet metal, (B and E) brass sheet metal, and (C and F) phosphor bronze-MDF. In panel C: black arrow, nanoflower; white arrow, nucleation site. Scale bar=2 μm; all figures are at the same scale.
Figure 3:
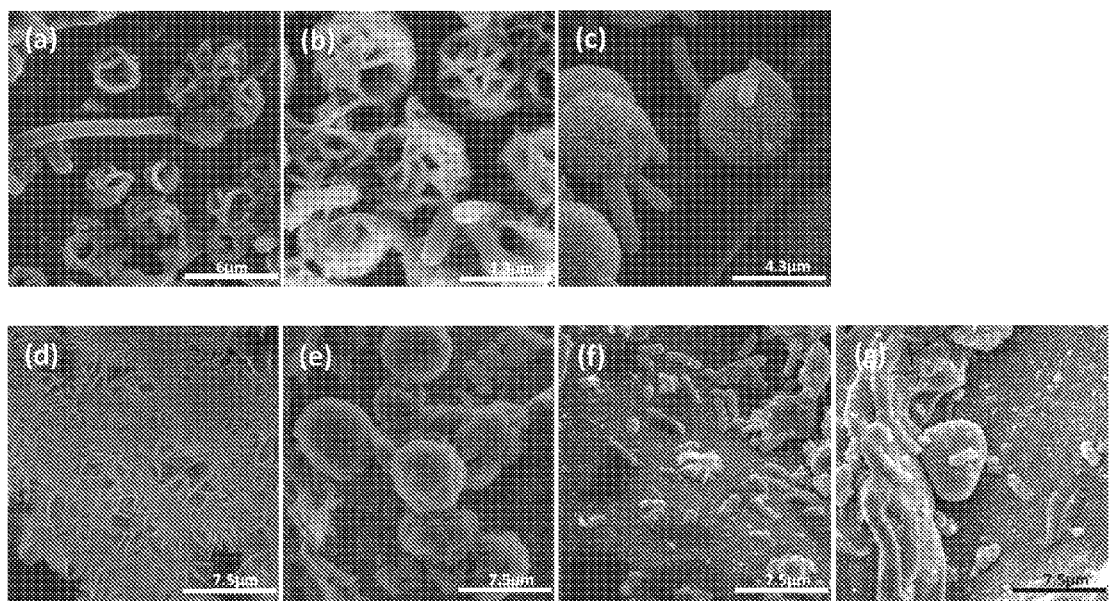
FIG. 3 shows a chronological progression of nanoflower formation. (a) 0.5 hours, (b) 1 hour, and (c) 2 hours. Effect of media and buffer on nanoflower formation. (d) PBS without bacteria, (e) PBS and LB broth without bacteria, (f) bacteria in 0.9% NaCl solution, and (g) bacteria in PBS with 10 mM EDTA.

A time course analysis revealed that petal-like structures are associated with the E. coli as early as 30 minutes of exposure (FIG. 3a), growing in size until reaching maximum size after two hours of incubation (FIGS. 3b and 3c). Rod-like extensions extending from the swollen E. coli cells likely represent sites of crystal nucleation (FIG. 2c) as they do not have the long, threadlike appearance of fimbriae/pili. In contrast to E. coli, no significant difference in size was noted in S. epidermidis exposed to the phosphor bronze coating, although cells with extensive membrane blebs were often noted (FIG. 2f). A minor subset of the cells with membrane blebs was associated with nanoflowers.

In order to determine whether nanoflower nucleation was mediated by organic components derived from killed bacteria, crystal formation was analyzed in the absence of bacteria. In the presence of PBS and the absence of bacteria, non-spherical, fibrous-like microcrystals were seen (FIG. 3d). In the presence of PBS and LB, without bacteria, non-porous formations with a mulberry-like surface topography were observed (FIGS. 2 and 3e). When saline was substituted for PBS, swollen bacteria were observed. However, nanoflowers, crystals, or evidence of biofilm formation was not observed (FIG. 3f). Likewise, nanoflowers and crystals were not observed following the chelation of copper ions with EDTA in the presence of PBS and bacteria (FIG. 3g). Thus nanoflowers formed only in the presence of PBS and bacteria, and were composed of protein-copper-phosphate crystals.

Discussion

Several studies have demonstrated that exposure of bacteria to copper alloys (>60% copper) for two hours at 37° C. results in the killing of approximately 90% of the bacteria [5]. Consistent with the inverse relationship between biocidal activity and copper content, the data obtained here indicate that 80% of the gram-negative E. coli and gram-positive S. epidermidis were killed when exposed for two hours at room temperature to brass sheet metal with 87% copper and 13% zinc content. The biocidal efficacy was increased by 10 to 15% when cells were exposed to phosphor bronze coatings with slightly higher copper content (91.7% copper). Unexpectedly, in contrast to control stainless steel and brass sheet metals, neither viable E. coli nor S. epidermidis were released from sanded and unsanded coatings despite rigorous washing in the presence of glass beads, which could have been attributed to different surface roughness. Analysis by epifluorescence microscopy revealed that the biocidal activity of brass sheet metal and the phosphor bronze coating had comparable biocidal activities despite the differences in surface roughness. Hence, the differential cell adhesion between brass sheet metal and phosphor bronze coatings was apparently due to a number of variables.

Adhesion of bacteria to abiotic surfaces involves a stereotypic series of steps. The first step involves a gravity-mediated association with abiotic surfaces, a process that is accelerated by flagellar movement [6]. The second step, adhesion, is promoted by several factors, such as the membrane composition of the bacteria, the presence of fimbriae/pili, the formation biofilm by bacterial aggregates, as well as the surface topography of the substrate. The transition during this second step from "reversible" to "non-reversible" adhesion can be triggered by the formation of biofilm by bacteria that have made contact with a solid substrate [6]. Furthermore, analysis of biofilm production by aggregates of the genetically tractable E. coli over abiotic surfaces is partly promoted by flagellated strains [7]. However, E. coli DH5α and S. epidermidis, which have no flagella, were found here to tightly adhere to phosphor bronze coating. Additionally, in contrast to the mainly amorphous appearance of extracellular polymeric biofilms observed under SEM that are formed by bacterial colonies [8], petal-like structures were in intimate contact with the swollen E. coli and a subset of S. epidermidis. Increase in biofilm mass is dependent on bacterial proliferation and the continuous recruitment of free-floating bacteria. Hence, the presence of biocidal levels of copper is likely to be refractory to the growth of biofilms. Although it cannot be discounted that biofilm may have formed that was undetectable by SEM, the combined data indicate that biofilm-mediated adhesion is unlikely to have made a significant contribution to the irreversible adhesion of E. coli and S. epidermidis to the phosphor bronze coating.

Although poorly understood, there is a growing body of evidence that sessile bacteria sense and respond to the topography of their microenvironments, promoting or decreasing their surface adhesion depending on the size, morphology and physiochemical properties of the bacteria. However, with respect to nanostructure surfaces, contradictory results have been reported on the impact of surface roughness and the number of bound bacteria. As reviewed by Anselme et al., the contradictory results in bacterial adhesion are due to a combination of differences in the chemistry, wettability and nanotopography of surfaces. To circumvent issues associated with the impact of variances in substrate chemistry, they investigated the adhesion of different bacteria on glass slides with distinctive degrees of surface roughness, but with no measurable differences in surface chemistry [9]. Their study demonstrated that E. coli attached readily to the smooth rather than rough glass surfaces. However, binding of the spherical S. aureus was not as affected by changes in surface roughness in the nano-scale range. Here, no significant difference in the number of E. coli and S. epidermidis bound to stainless steel with a $R_a$ value of 180 nm was observed. Approximately 50% more bacteria were associated with the brass sheet metal with a $R_a$ value of 540 nm than with stainless steel. SEM images revealed that the surface of both bacterial species appeared rougher when exposed to brass sheet metal. The change in membrane morphology, combined with the rougher surface of brass sheet metal, may have resulted in a higher number of bacteria being retained on brass sheet metal compared to stainless steel.

A striking difference in bacterial morphology was observed between the solid metals and the phosphor bronze coating. This was particularly evident for E. coli cells that were approximately 3 to 4 fold larger with compromised membranes when plated on the sanded and unsanded phosphor bronze coating. The increased swelling in the presence of a hypotonic PBS solution may reflect that the cell walls of the bacteria were compromised by the copper ions. Swelling was observed after only 30 minutes of exposure to the biocidal surface, indicating that aberrant membrane permeability occurred rapidly, leading to osmotic stress due to the influx of water. Whether the cell walls were damaged by the generation of hydroxyl free radicals by Haber-Weiss and Fenton reactions of reduced copper ions remains to be determined. It is also likely that E. coli genomic material was also rapidly degraded by the resultant free radicals as demonstrated for E. coli by Espirito Santo et al [10]. As noted by Warnes et al [11], propidium iodide does not effectively bind to degraded DNA. It is, therefore possible that a subset of the E. coli on brass sheet metal and the phosphor bronze coating may not have been stained with propidium iodide, leading to an underestimate of biocidal efficacy. Moreover, intact bacteria with degraded DNA would have been non-viable, which may have affected the viable cell count for E. coli incubated on brass sheet metal.

No significant difference in the size of gram-positive S. epidermidis was observed by exposure to all substrates used here. Warnes et al. did not observe a change in the size and membrane morphology of gram-positive Enterococcus faecalis and Enterococcus faecium when exposed to copper alloys with a copper content ranging from 60-95%. Bacterial killing was attributed to an inhibition of cellular respiration and DNA degradation by reactive oxygen species (ROS). In contrast to the observations made here, with S. epidermidis where viable cells were detectable after two hours of exposure to brass sheet metal, no viable E. faecalis and E. faecium cells were observed after one hour exposure to the copper alloys. As the authors hypothesized, it is conceivable that for gram-positive cells the absence of an outer cell wall and periplasmic space facilitates the intracellular penetration of toxic ROS, leading to cell death with minimum impact on cell membrane. The results here indicate that a subset of the S. epidermidis had compromised cell membranes when exposed to phosphor bronze coating, possibly reflecting species-specific differences in the response of gram-positive cells to toxic levels of copper, or that macro scale differences between peaks and valleys enhances bacterial killing by increasing the concentration of copper within the valleys where the majority of cells were observed. It was also observed here that a subset of the S. epidermidis with membrane blebs were also associated with nanoflowers in the presence of PBS, indicating the organic material released from the damaged cells promoted the nucleation of organic-copper-phosphate crystals.

The formation of nanoflowers following the exposure of bacteria to the phosphor bronze coating was not expected. The observed spheres were remarkably similar in appearance and size to nanoflowers that were self-assembled in the presence of polypeptides, $CuSO_4$ and PBS pH 7.4 after 3 days of incubation [3]. In this case, however, primary crystals were visible as early as 30 minutes, reaching, within two hours, a size comparable to those formed with purified proteins after three days. It is possible that a complex mixture of organic compounds derived from bacteria and a high accumulation of copper ions within the valleys where cells were concentrated greatly augmented the rate of crystal nucleation. Consistent with a nucleation role by bacteria-derived components, membrane disruption was also evident after only 30 minutes of incubation. The combined data indicate that a change from nanoscale to macroscale topography has pronounced impact on the biocidal efficacy of copper alloys.

The gram-negative bacteria used the examples is E. coli, but other gram-negative bacteria are known, and would be expected to be useful in the production of nanoflowers.

As mentioned above, nanoflowers obtained herein had a typical overall spherical shape with diameters in the range of about 3.5 to 5 µm. As indicated in the results obtained, the size of nanoflower obtainable is time dependent, so other sizes can be obtained.

Applications

Nanoflowers can be synthesized for various uses.

In one approach, a biosensor is created by producing a nanoflower under conditions such as those described herein and in which the growth milieu contains an enzyme or other protein to be incorporated as part of the nanoflower. Examples of suitable enzymes are described by Ge [3]: laccase, for the detection of a phenolic compound such as epinephrine, norepinephrine or dopamine; α-lactalbumin; carbonic anhydrase; or lipase. In this way, functionalized nanoflowers are created at a relatively rapid rate.

The disclosures of all references mentioned herein are incorporated herein by reference as though those disclosures were reproduced in this specification in their entirety.

REFERENCES

1. Ho W. H., et al. Three-dimensional crystalline SiC nanowire flowers. Nanotechnology 2004; 15:996.
2. Peng et al., United States Patent Publication No. 2008/0081016, published Apr. 3, 2008.
3. Ge J., Lei J., and Zare R. 2012. Protein-inorganic hybrid nanoflowers. Nature Nanotechnology. 7:428-432.
4. Pershin et al., United States Patent Publication No. 2011/0171396 published Jul. 14, 2011.
5. Grass, G., Rensing C., and Solioz M. Metallic copper as an antimicrobial surface. Applied and Environmental Microbiology 2011; 77: 1541-1547.
6. Anselme K., Davidson P., Popa A M., Giazzon M., Liley M., and Ploux L. 2010. The interaction of cells and bacteria with surfaces structured at the nanometre scale. Acta Biomater. 10; 3824-3846.
7. Pratt L. A. and Kolter R. 1998. Genetic analysis of Escherichia coli biofilm formation: roles of flagella, motility, chemotaxis and type I pili. Molecular Microbiology. 30:285-93.
8. Flemming H. C and Wingender J. 2010. The biofilm matrix. Nature Reviews Microbiology. 8(9):623-633.
9. Mitik-Dineva N., Wang J., Truong V K., Stoddart P., Malherbe F., Crawford R J., and Ivanova EP. 2009. Escherichia coli, Pseudomonas aeruginosa and Staphylococcus aureus Attachment Patterns on Glass Surfaces with Nanoscale Roughness. Current Microbiology. 58: 268-273.
10. Espirito Santo, C. et al. Contribution of copper ion resistance to survival of Escherichia coli on metallic copper surfaces. Applied and Environmental Microbiology. 2008; 74:977-986.
11. Warnes, S. L. Biocidal efficacy of copper alloys against pathogenic enterococci involves degradation of genomic and plasmid DNAs. Applied and Environmental Microbiology 2010; 5390-5401.

What is claimed is:

1. A composite material comprising a nanoflower and bacterium, wherein at least a portion of the bacterium is embedded in the nanoflower.

2. The composite material of claim 1, wherein bacterium is gram-negative.

3. The composite material of claim 1, wherein the nanoflower comprises copper phosphate.

4. The composite material of claim 3, wherein the material is anchored to a substrate wherein the substrate comprises a copper alloy.

5. The composite material of claim 4, wherein the substrate comprises an alloy of copper and tin, and phosphorus, comprising between 5% and 40% tin by weight, between 60% and 95% copper by weight, and between 0.5% and 2% phosphorus by weight, a surface of the substrate has a surface roughness, $R_a$, from about 1 µm to about 10 µm and a maximum valley profile depth $R_v$ of no greater than about 30 µm.

6. The composite material of claim 1, further comprising an enzyme anchored to the nanoflower.

7. The composite material of claim 6, wherein the enzyme is selected from the group consisting of laccase, α-lactalbumin, carbonic anhydrase and lipase.

\* \* \* \* \*